United States Patent
Yamano et al.

(10) Patent No.: US 10,591,347 B2
(45) Date of Patent: Mar. 17, 2020

(54) METHOD FOR MEASURING BASIS WEIGHT, METHOD FOR MANUFACTURING LAMINATED FILM, AND DEVICE FOR MEASURING BASIS WEIGHT

(71) Applicant: Sumitomo Chemical Company, Limited, Tokyo (JP)

(72) Inventors: Takayuki Yamano, Niihama (JP); Takahiro Okugawa, Niihama (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 220 days.

(21) Appl. No.: 15/579,991

(22) PCT Filed: Jun. 2, 2016

(86) PCT No.: PCT/JP2016/066484
§ 371 (c)(1),
(2) Date: Dec. 6, 2017

(87) PCT Pub. No.: WO2016/199683
PCT Pub. Date: Dec. 15, 2016

(65) Prior Publication Data
US 2018/0172499 A1    Jun. 21, 2018

(30) Foreign Application Priority Data

Jun. 11, 2015   (JP) ................. 2015-118700

(51) Int. Cl.
*G01G 9/00* (2006.01)
*G01B 11/06* (2006.01)
(Continued)

(52) U.S. Cl.
CPC ............. *G01G 9/005* (2013.01); *C23C 26/00* (2013.01); *G01B 11/06* (2013.01); *G01G 7/02* (2013.01);
(Continued)

(58) Field of Classification Search
CPC .......... G01G 9/005; C23C 26/00; G01B 11/06
See application file for complete search history.

(56) References Cited

U.S. PATENT DOCUMENTS

| 2004/0239919 | A1 | 12/2004 | Schwarz |
| 2010/0159121 | A1* | 6/2010 | Meijer Drees ......... G01B 15/00 427/8 |
| 2010/0259748 | A1 | 10/2010 | Suzuki |

FOREIGN PATENT DOCUMENTS

| CN | 201707033 U | 1/2011 |
| JP | H04355308 A | 12/1992 |

(Continued)

OTHER PUBLICATIONS

Office Action dated Mar. 21, 2019 in CN Application No. 201680033641.4.

(Continued)

*Primary Examiner* — Austin Murata
(74) *Attorney, Agent, or Firm* — Panitch Schwarze Belisario & Nadel LLP

(57) ABSTRACT

To measure the mass per unit area of an applied layer in a layered film while preventing a measurement error from being caused by thickness unevenness, a per-unit-area-mass measuring device (30) includes a light projector (31a) configured to project light having a center wavelength of 405 nm, a light projector (31b) configured to project light having a center wavelength of 850 nm, light receivers (32a, 32b) configured to receive light having been transmitted through a separator (12), and a control section (33) configured to calculate the mass per unit area of a heat-resistant layer (4) on the basis of the respective transmitted-light intensities of the light having a center wavelength of 405 nm and the light having a center wavelength of 850 nm.

10 Claims, 11 Drawing Sheets

(51) Int. Cl.
    *G01G 17/04*      (2006.01)
    *C23C 26/00*      (2006.01)
    *G01G 7/02*       (2006.01)
    *G01N 21/25*      (2006.01)
    *G06F 17/11*      (2006.01)

(52) U.S. Cl.
    CPC ........... *G01G 17/04* (2013.01); *G01N 21/251* (2013.01); *G06F 17/11* (2013.01)

(56)         References Cited

FOREIGN PATENT DOCUMENTS

| JP | H09178433 A   | 7/1997  |
|----|---------------|---------|
| JP | H11118434 A   | 4/1999  |
| JP | H11153417 A   | 6/1999  |
| JP | 2003075126 A  | 3/2003  |
| JP | 2004205696 A  | 7/2004  |
| JP | 2004333494 A  | 11/2004 |
| JP | 2008058257 A  | 3/2008  |
| JP | 2009133725 A  | 6/2009  |
| JP | 2010-101866 A | 5/2010  |

OTHER PUBLICATIONS

Int'l Preliminary Report on Patentability dated Dec. 12, 2017 in Int'l Application No. PCT/JP2016/066484.
Int'l Search Report dated Jul. 5, 2016 in Int'l Application No. PCT/JP2016/066484.
Office Action dated Jun. 4, 2019 in JP Application No. 2015118700 (Partial English Translation).
Office Action dated Jan. 8, 2019 in JP Application No. 2015-118700.

\* cited by examiner

METHOD FOR MEASURING BASIS WEIGHT, METHOD FOR MANUFACTURING LAMINATED FILM, AND DEVICE FOR MEASURING BASIS WEIGHT

CROSS-REFERENCE TO RELATED APPLICATION

This application is a section 371 of international application no. PCT/JP2016/066484, filed Jun. 2, 2016, which was published in the Japanese language on Dec. 15, 2016, under international publication no. WO 2016/199683 A1, which claims the benefit to Japanese Application No. 2015-118700, filed Jun. 11, 2015, the entire disclosures of all of which are incorporated herein by reference.

TECHNICAL FIELD

The present invention relates to (i) a method for measuring a mass per unit area of an applied layer in a layered film including a base film and an applied layer provided on the base film, (ii) a method for producing a layered film, and (iii) a device for measuring a mass per unit area of an applied layer.

BACKGROUND ART

In the field of a magnetic recording medium, Patent Literature 1 discloses a technique for measuring the respective thicknesses of a first layer on a base film and a second layer above the base film. This technique includes causing two kinds of light having respective center wavelengths different from each other to be transmitted through a magnetic recording medium including a base film, a first layer, and a second layer to calculate the respective thicknesses of the first layer and the second layer from the respective intensities of the two kinds of transmitted light.

CITATION LIST

Patent Literature

[Patent Literature 1]
Japanese Patent Application Publication Tokukaihei No. 9-178433 (Publication date: Jul. 11, 1997)

SUMMARY OF INVENTION

Technical Problem

In the technical field of a layered film including a base film and an applied layer provided on the base film, it is preferable to be capable of measuring a mass of the applied layer per unit area. The technique of Patent Literature 1 is, unfortunately, not sufficiently accurate in measurement of a mass per unit area for the reason discussed below.

The technique of Patent Literature 1 includes measuring in advance the thickness of a base film equivalent to the base film in the magnetic recording medium to calculate the respective thicknesses of the first layer and the second layer. The base film in the layered film is, however, uneven in thickness. A base film formed through a stretching step is particularly uneven in thickness. A porous film such as a base film in a battery separator, in particular, is greatly uneven in thickness as compared with a non-porous base film. Even in the case where the thickness of a base film equivalent to the base film in the magnetic recording medium is measured in advance and a mass per unit area of the applied layer is calculated from the measurement value, there will unfortunately be a great error between the calculated mass per unit area and the actual mass per unit area.

The present invention has been accomplished in view of the above problem. It is an object of an embodiment of the present invention to measure the mass per unit area of an applied layer in a layered film while preventing a measurement error such as the above from being caused by unevenness in the thickness of a base film in the layered film.

Solution to Problem

In order to attain the above object, a method of an embodiment of the present invention for measuring a mass per unit area is a method for measuring a mass per unit area of an applied layer in a layered film including a base film and the applied layer provided on the base film, the method including: a light-transmitting step of causing measurement light to be transmitted through the layered film, the measurement light including a first beam having a center wavelength at a first wavelength and a second beam having a center wavelength at a second wavelength different from the first wavelength; a light-measuring step of measuring respective transmitted-light intensities of the first and second beams of the measurement light having been transmitted through the layered film; and a calculating step of calculating the mass per unit area of the applied layer on a basis of the transmitted-light intensities.

Further, a method of an embodiment of the present invention for measuring a mass per unit area is a method for measuring a mass per unit area of an applied layer in a layered film including a base film and the applied layer provided on the base film, the method including: a light-transmitting step of causing measurement light to be transmitted through the layered film; a light-measuring step of (i) separating, into a first beam having a first wavelength and a second beam having a second wavelength different from the first wavelength, the measurement light having been transmitted through the layered film and (ii) measuring respective transmitted-light intensities of the first and second beams; and a calculating step of calculating the mass per unit area of the applied layer on a basis of the transmitted-light intensities.

A method of an embodiment of the present invention for producing a layered film is a method for producing a layered film including a base film and an applied layer on the base film, the method including: each step included in any method above; and a coating step of controlling the mass per unit area of the applied layer on a basis of the mass per unit area which mass has been calculated in the calculating step.

Further, a method of an embodiment of the present invention for producing a layered film is a method for producing a layered film including a base film and an applied layer on the base film, the method including: each step included in any method above; and a removing step of removing a per-unit-area-mass abnormal portion of the layered film on a basis of the mass per unit area which mass has been calculated in the calculating step.

A device of an embodiment of the present invention for measuring a mass per unit area is a device for measuring a mass per unit area of an applied layer in a layered film including a base film and the applied layer provided on the base film, the device including: two light projectors, a first one of the two light projectors being configured to project a first beam of measurement light which first beam has a center wavelength at a first wavelength, a second one of the two light projectors being configured to project a second beam of the measurement light which second beam has a center wavelength at a second wavelength different from the first wavelength; two light receivers, a first one of the two light receivers being configured to measure a transmitted-light intensity of the first beam of the measurement light having been transmitted through the layered film, a second one of the two light receivers being configured to measure a transmitted-light intensity of the second beam of the measurement light having been transmitted through the layered film; and a calculating section configured to calculate the mass per unit area of the applied layer on a basis of the transmitted-light intensities.

Further, a device of an embodiment of the present invention for measuring a mass per unit area is a device for measuring a mass per unit area of an applied layer in a layered film including a base film and the applied layer provided on the base film, the device including: a light projector configured to project measurement light; a spectrometer section configured to (i) separate, into a first beam having a first wavelength and a second beam having a second wavelength different from the first wavelength, the measurement light having been transmitted through the layered film and (ii) measure respective transmitted-light intensities of the first and second beams; and a calculating section configured to calculate the mass per unit area of the applied layer on a basis of the transmitted-light intensities.

Advantageous Effects of Invention

An embodiment of the present invention advantageously makes it possible to measure the mass per unit area of an applied layer in a layered film while preventing a measurement error such as the above from being caused by unevenness in the thickness of a base film in the layered film. Further, an embodiment of the present invention advantageously makes it possible to (i) produce a layered film including an applied layer having a more uniform mass per unit area and (ii) improve the yield of a layered film.

DESCRIPTION OF EMBODIMENTS

[Basic Configuration]

An embodiment of the present invention allows for measurement of a mass per unit area of such layered films as an optical film and a secondary battery separator. The present invention is not intended to measure a per-unit-area mass of any film through which no light is transmitted such as a metal film.

Regarding a secondary battery separator, the description below deals sequentially with a lithium-ion secondary battery, a separator, a heat-resistant separator, a method for producing a separator/heat-resistant separator, and slitting as a basic configuration.

(Lithium Ion Secondary Battery)

A nonaqueous electrolyte secondary battery, typically, a lithium-ion secondary battery has a high energy density, and therefore, currently widely used not only as batteries for use in devices such as personal computers, mobile phones, and mobile information terminals, and for use in moving bodies such as automobiles and airplanes, but also as stationary batteries contributing to stable power supply.

Figure 1:
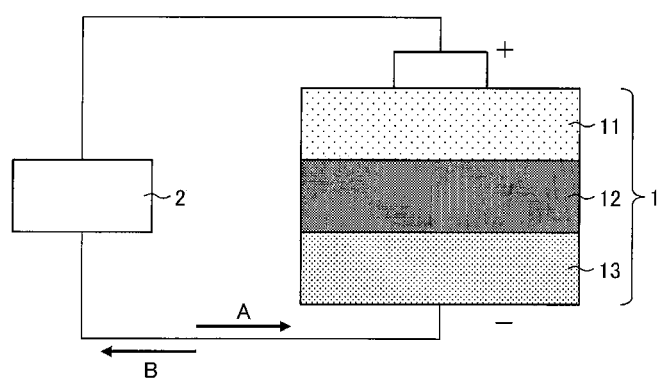
FIG. 1 is a diagram schematically illustrating a cross-sectional configuration of a lithium-ion secondary battery.

FIG. 1 is a diagram schematically illustrating a cross-sectional configuration of a lithium-ion secondary battery 1 (battery).

As illustrated in FIG. 1, the lithium-ion secondary battery 1 includes a cathode 11, a separator 12 (battery separator), and an anode 13. Between the cathode 11 and the anode 13, an external device 2 is connected outside the lithium-ion secondary battery 1. Then, while the lithium-ion secondary battery 1 is being charged, electrons move in a direction A. On the other hand, while the lithium-ion secondary battery 1 is being discharged, electrons move in a direction B.

(Separator)

The separator 12 is provided so as to be sandwiched between the cathode 11 which is a positive electrode of the lithium-ion secondary battery 1 and the anode 13 which is a negative electrode of the lithium-ion secondary battery 1. The separator 12 is a porous film (base film) which separates the cathode 11 and the anode 13, allowing lithium ions to move between the cathode 11 and the anode 13. The separator 12 contains, for example, polyolefin such as polyethylene or polypropylene as a material.

Figure 2:
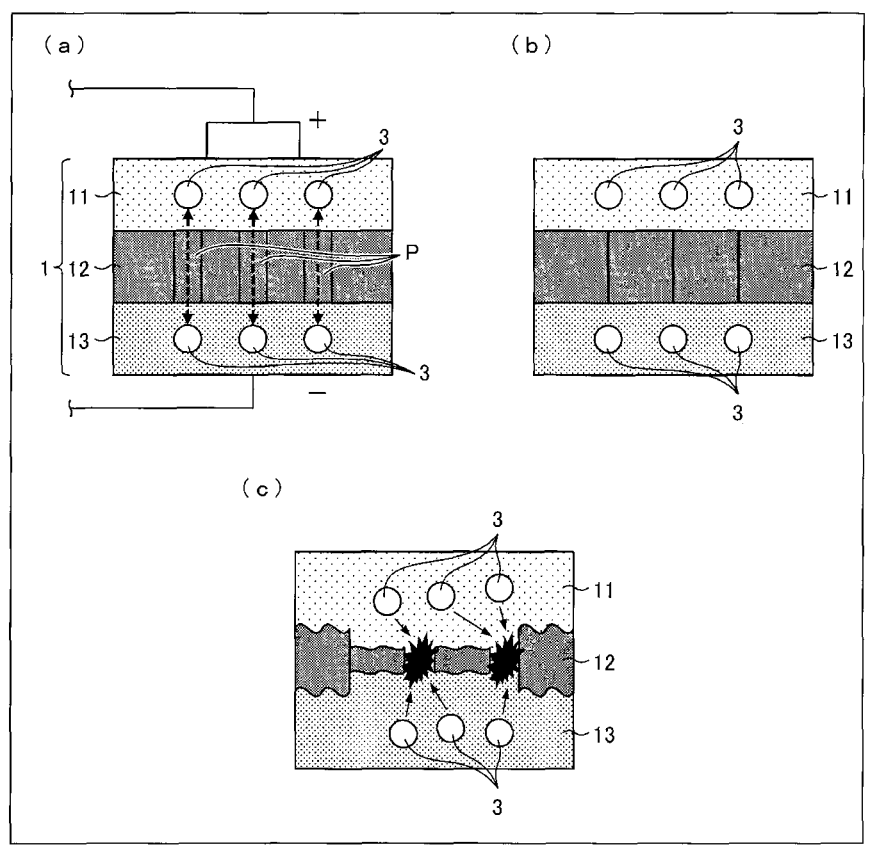
FIG. 2 provides diagrams each schematically illustrating details of the configuration of the lithium-ion secondary battery illustrated in FIG. 1.

FIG. 2 provides diagrams each schematically illustrating details of the configuration of the lithium-ion secondary battery 1 illustrated in FIG. 1. (a) of FIG. 2 illustrates a normal configuration. (b) of FIG. 2 illustrates a state in which a temperature of the lithium-ion secondary battery 1 has risen. (c) of FIG. 2 illustrates a state in which a temperature of the lithium-ion secondary battery 1 has sharply risen.

As illustrated in (a) of FIG. 2, the separator 12 is provided with many pores P. Normally, lithium ions 3 in the lithium-ion secondary battery 1 can move back and forth through the pores P.

However, there are, for example, cases in which the temperature of the lithium-ion secondary battery 1 rises due to excessive charging of the lithium-ion secondary battery 1, a high current caused by short-circuiting of the external device, or the like. In such cases, the separator 12 melts or softens and the pores P are blocked as illustrated in (b) of FIG. 2. As a result, the separator 12 shrinks. This stops the movement of the lithium ions 3, and consequently stops the above temperature rise.

However, in a case where a temperature of the lithium-ion secondary battery 1 sharply rises, the separator 12 suddenly shrinks. In this case, as illustrated in (c) of FIG. 2, the separator 12 may be broken. Then, the lithium ions 3 leak out from the separator 12 which has been broken. As a result, the lithium ions 3 do not stop moving. Consequently, the temperature continues rising.

(Heat-Resistant Separator)

Figure 3:
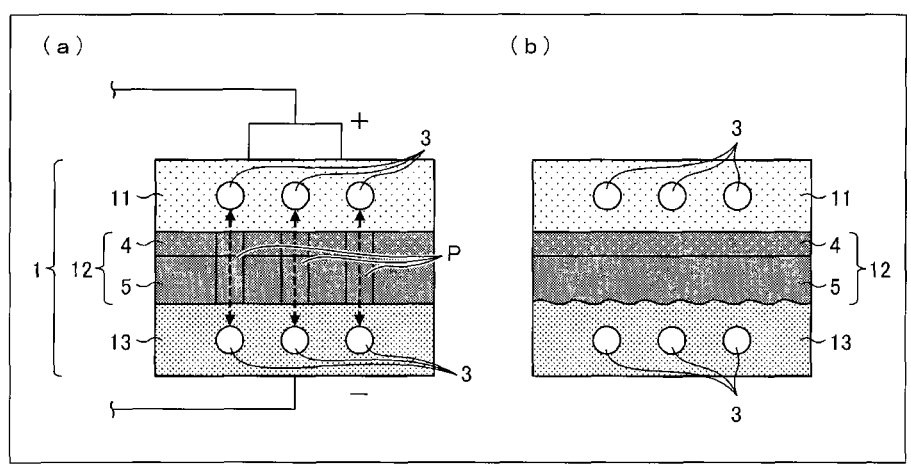
FIG. 3 provides diagrams schematically illustrating another configuration of the lithium-ion secondary battery illustrated in FIG. 1.

FIG. 3 provides diagrams schematically illustrating another configuration of the lithium-ion secondary battery 1 illustrated in FIG. 1. (a) of FIG. 3 illustrates a normal configuration, and (b) of FIG. 3 illustrates a state in which a temperature of the lithium-ion secondary battery 1 has sharply risen.

As illustrated in (a) of FIG. 3, the separator 12 can be a heat-resistant separator that includes a base film 5 and a heat-resistant layer (applied layer) 4. The heat-resistant layer 4 is disposed on a surface of the base film 5 which surface is on a cathode 11 side. Note that the heat-resistant layer 4 can alternatively be disposed on a surface of the base film 5 which surface is on an anode 13 side, or both surfaces of the base film 5. Further, the heat-resistant layer 4 is provided with pores which are similar to the pores P. Normally, the lithium ions 3 move back and forth through the pores P and the pores of the heat-resistant layer 4. The heat-resistant layer 4 contains, for example, wholly aromatic polyamide (aramid resin) as a material.

As illustrated in (b) of FIG. 3, even in a case where the temperature of the lithium-ion secondary battery 1 sharply rises and as a result, the base film 5 melts or softens, the shape of the base film 5 is maintained because the heat-resistant layer 4 supports the base film 5. Therefore, such a sharp temperature rise results in only melting or softening of the base film 5 and consequent blocking of the pores P. This stops movement of the lithium ions 3 and consequently stops the above-described excessive discharging or excessive charging. In this way, the separator 12 can be prevented from being broken.

(Steps of Producing Separator, Heat-Resistant Separator)

How to produce the separator and heat-resistant separator of the lithium-ion secondary battery 1 is not specifically limited. The heat-resistant separator 12a can be produced by a well-known method. The following discussion assumes a case where the base film 5 contains polyethylene as a main material. However, even in a case where the base film 5 contains another material, the similar steps can still be applied to production of the separator 12 (heat-resistant separator).

For example, it is possible to employ a method including the steps of first forming a film by adding an inorganic filler or plasticizer to a thermoplastic resin, and then washing the film with an appropriate solvent to remove the inorganic filler or plasticizer. For example, in a case where the base film 5 is a polyolefin separator made of a polyethylene resin containing ultrahigh molecular weight polyethylene, it is possible to produce the separator 12 by the following method.

This method includes (1) a kneading step of obtaining a polyethylene resin composition by kneading an ultrahigh molecular weight polyethylene and an inorganic filler (for example, calcium carbonate or silica) or plasticizer (for example, a low molecular weight polyolefin or liquid paraffin), (2) a rolling step of forming a film with the polyethylene resin composition, (3) a removal step of removing the inorganic filler or plasticizer from the film obtained in the step (2), and (4) a stretching step of obtaining the base film 5 by stretching the film obtained in the step (3). The step (4) may alternatively be carried out between the steps (2) and (3).

In the removal step, many fine pores are provided in the film. The fine pores of the film stretched in the stretching step become the above-described pores P. The base film 5 formed as a result is a polyethylene microporous film having a prescribed thickness and a prescribed air permeability (that is, a separator 12 not having a heat-resistant layer [applied layer]).

Note that in the kneading step, 100 parts by weight of the ultrahigh molecular weight polyethylene, 5 parts by weight to 200 parts by weight of a low-molecular weight polyolefin having a weight-average molecular weight of not more than 10000, and 100 parts by weight to 400 parts by weight of the inorganic filler can be kneaded.

Thereafter, in a coating step, the heat-resistant layer 4 is formed on a surface of the base film 5. For example, on the base film 5, an aramid/NMP (N-methylpyrrolidone) solution (coating solution) is applied, and thereby, the heat-resistant layer 4 that is an aramid heat-resistant layer is formed. The heat-resistant layer 4 can be provided on only one surface or both surfaces of the base film 5. Alternatively, the heat-resistant layer 4 can be formed by using a mixed solution containing a filler such as alumina/carboxymethyl cellulose for coating.

In the coating step, a polyvinylidene fluoride/dimethylacetamide solution (coating solution) may be applied (applying step) to a surface of the base film 5 and solidified (solidifying step) to form an adhesive layer (applied layer) on the surface of the base film 5. The adhesive layer can be provided on only one surface or both surfaces of the base film 5.

A method for coating the base film 5 with a coating solution is not specifically limited as long as uniform wet coating can be performed by the method. The method can be a conventionally well-known method such as a capillary coating method, a spin coating method, a slit die coating method, a spray coating method, a dip coating method, a roll coating method, a screen printing method, a flexo printing method, a bar coater method, a gravure coater method, or a die coater method. The heat-resistant layer 4 has a thickness which can be controlled by adjusting a thickness of a coating wet film and/or a solid-content concentration in the coating solution.

It is possible to use a resin film, a metal belt, a drum or the like as a support with which the base film 5 is fixed or transferred in coating.

As described above, it is possible to produce the separator 12 (heat-resistant separator) in which the heat-resistant layer 4 is laminated on the base film 5. Thus produced separator is wound on a cylindrical core. Note that a subject to be produced by the above production method is not limited to the heat-resistant separator. The above production method does not necessarily include the coating step. In a case where the method includes no coating step, the subject to be produced is a separator having no heat-resistant layer. It is also possible to produce an adhesive separator having an applied layer (for example, an adhesive layer described later) other than a heat-resistant layer by a method similar to the method for producing a heat-resistant separator.

(Slitting)

The heat-resistant separator or the separator having no heat-resistant layer (hereinafter, referred to as "separator") preferably has a width (hereinafter, referred to as "product width") suitable for application products such as the lithium-ion secondary battery 1. However, for improving productivity, the separator is produced so as to have a width that is equal to or larger than a product width. Then, after having been once produced so as to have a width equal to or larger than the product width, the separator is slit into a separator(s) having the product width.

Note that the "separator width" means a dimension of the separator in a direction substantially perpendicular to a lengthwise direction and a thickness direction of the separator. In the description below, a wide separator having not yet been slit is referred to as an "original sheet" while particularly a separator having been slit is referred to as a "slit separator". Moreover, "slit" means to cut off a separator in a lengthwise direction (i.e., a direction in which a film flows in production, MD: machine direction), and "cut" means to cut the separator in a transverse direction (TD). The transverse direction (TD) means a direction that is substantially perpendicular to the lengthwise direction (MD) and the thickness direction of the separator.

Embodiments

An embodiment of the present invention is described below with reference to FIGS. 4 through 12.

«Steps Related to Applied Layer»

Figure 4:
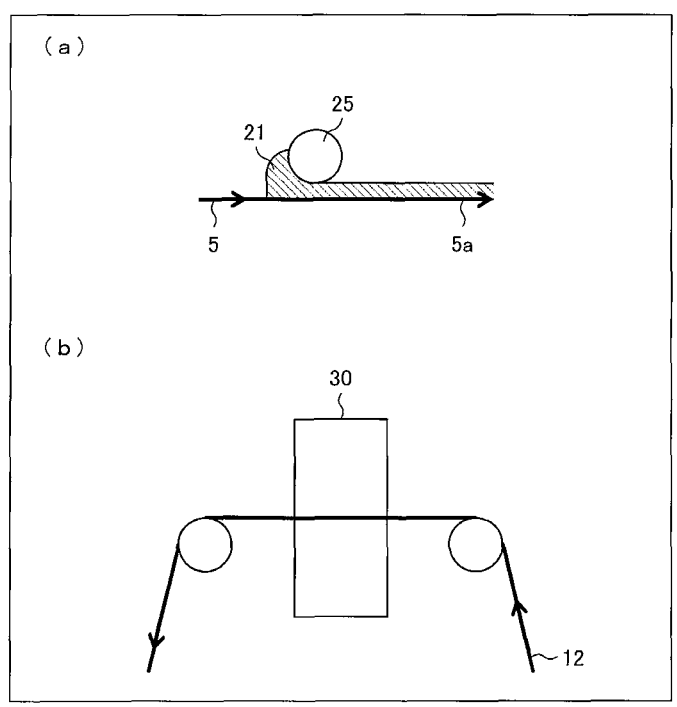
FIG. 4 provides diagrams each schematically illustrating a step related to an applied layer which step is included in a method of an embodiment of the present invention for producing a layered film.

FIG. 4 provides diagrams each schematically illustrating a step related to an applied layer which step is included in a method of the present embodiment for producing a laminated film, where (a) of FIG. 4 illustrates a coating step, and (b) of FIG. 4 illustrates an inspecting step.

The description below deals with, as a typical embodiment of the present invention, a method for producing a separator 12 as an example.

(Coating Step)

The coating step illustrated in (a) of FIG. 4 is, as described above, a step of coating the base film 5 with a composition (hereinafter referred to as "coating solution") prepared by mixing with a solvent a substance (hereinafter referred to as "applied-layer substance") to be included in a heat-resistant layer 4 as an applied layer for the separator 12. The applied-layer substance may alternatively be a substance to be included in an adhesive layer described above. The base film 5 is coated with the coating solution 21 with use of a coating member 25.

The base film 5 coated with the coating solution 21 (hereinafter referred to as "base film 5a") is subjected to a drying step, and is then transferred to an inspecting step described later. The base film 5a may be transferred to a depositing step and a washing step (solvent replacing step) before being transferred to the drying step. The depositing step is a step of depositing the applied-layer substance. The washing step is a step of washing the solvent away from the surface of the base film 5a with use of a cleaning liquid to replace the solvent in the pores with the cleaning liquid. The drying step is, (i) in a case where the base film 5a is not subjected to the washing step, a step of drying the base film 5a to remove the solvent on the surface and in the pores of the base film 5a and (ii) in a case where the base film 5a is subjected to the washing step, a step of drying the base film 5a to remove the cleaning liquid on the surface and in the pores of the base film 5a. The base film 5a, through the above steps, provides a separator 12 which includes a base film 5 and a heat-resistant layer 4 provided on the base film 5 and from which the solvent has been removed sufficiently. The separator 12 is then transferred to an inspecting step.

(Inspecting Step)

The inspecting step illustrated in (b) of FIG. 4 is a step of inspecting the separator 12 after the coating step. The separator 12 is inspected with use of a per-unit-area-mass measuring device 30.

The per-unit-area-mass measuring device 30 measures the mass of the heat-resistant layer 4 per unit area. An embodiment of the present invention has a main feature in the configuration of the per-unit-area-mass measuring device 30 as described later.

The applied layer (that is, a heat-resistant layer or an adhesive layer) for the separator 12 may be provided on both surfaces of the base film 5.

«Method for Measuring Mass Per Unit Area»

The mass of an applied layer per unit area is proportional to the absorbance of the applied layer. This proportional relation can be utilized to measure a mass per unit area. The term "absorbance" refers to a value calculated by $-\log(I/Iin)$, where Iin represents an incident light intensity, that is, the intensity of light entering an applied layer, and I represents a transmitted-light intensity, that is, the intensity of the above light having been transmitted through the applied layer. The description below deals with measurement of a mass per unit area for a case where (i) the base film 5 of the separator 12 contains polyethylene as a main component and (ii) the heat-resistant layer 4 (applied layer) contains aramid.

(Relation Between Wavelength and Absorbance)

Figure 5:
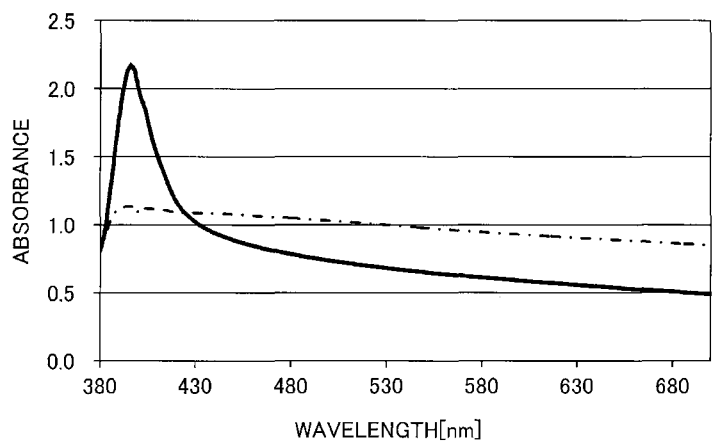
FIG. 5 is a graph illustrating a relation between (i) the wavelength of light with which a separator is irradiated and (ii) the absorbance for the light.

FIG. 5 is a graph illustrating a relation between (i) the wavelength of light with which the separator 12 is irradiated and (ii) the absorbance for the light (hereinafter referred to as "absorbance wavelength dependence"). The graph shows (i) a bold solid line to indicate the absorbance wavelength dependence of aramid and (ii) a dotted-and-dashed line to indicate the absorbance wavelength dependence of polyethylene. The absorbance wavelength dependence varies according to the proportion of resin contained in each layer included in the separator 12. In a case where, for example, the applied layer contains 50% by weight of a filler, the amount of resin contained corresponds to half the total amount, with the result that the absorbance of the applied layer is halved. Further, in a case where a layered film to be produced is a porous body such as the separator 12, it is necessary to consider light scattering caused by the pore structure. Thus, the absorbance wavelength dependence of each layer included in a layered film is desirably determined with reference to a single-layer film having a similar porous structure in terms of the pore size, the pore size distribution, and/or the like.

As illustrated in FIG. 5, in the case where the substance irradiated with light is aramid, the absorbance for light (measurement light) having a wavelength of not less than 390 nm and not more than 420 nm (first wavelength) is higher than that for light (measurement light) having a wavelength of not less than 680 nm and not more than 700 nm (second wavelength). In the case where the substance irradiated with light is polyethylene, the absorbance for light having a wavelength of not less than 390 nm and not more than 420 nm is equivalent to that for light having a wavelength of not less than 680 nm and not more than 700 nm. The absorbance wavelength dependence for light having a wavelength of more than 700 nm is similar (not shown in FIG. 5) to that for light having a wavelength of not less than 680 nm and not more than 700 nm. This indicates that aramid has an absorbance that depends on the wavelength and that polyethylene has an absorbance that does not tend to depend on the wavelength.

(Relation Between Mass Per Unit Area and Absorbance)

Figure 6:
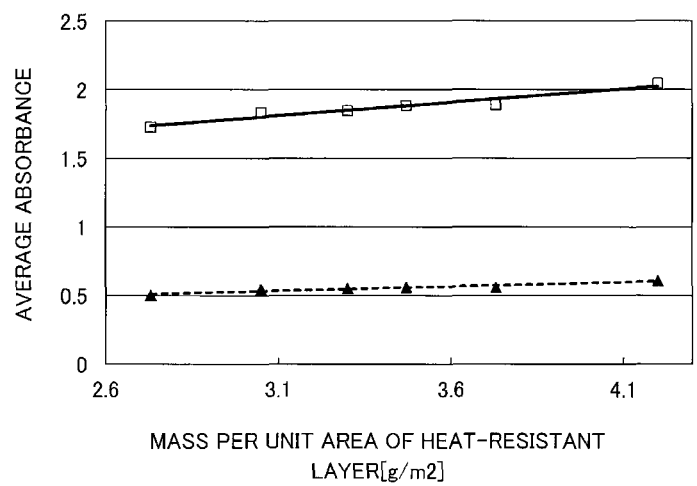
FIG. 6 is a graph illustrating a relation between (i) the mass per unit area of an applied layer (heat-resistant layer) in a separator and (ii) the average absorbance of the applied layer.

FIG. 6 is a graph illustrating a relation between (i) the mass per unit area of the heat-resistant layer 4 in the separator 12 and (ii) the average absorbance of the heat-resistant layer 4 (hereinafter referred to as "per-unit-area-mass absorbance correlation"). The graph shows (i) hollow squares representing data of a per-unit-area-mass absorbance correlation for light having a wavelength of not less than 390 nm and not more than 420 nm and (ii) triangles representing data of a per-unit-area-mass absorbance correlation for light having a wavelength of not less than 680 nm and not more than 700 nm.

The absorbance shown in FIG. 6 is a value calculated by $-\log(I/I_{in})$, where $I_{in}$ represents an incident light intensity, that is, the intensity of light entering a sample including (i) a glass substrate and (ii) a heat-resistant layer that contains aramid and alumina and that is provided on the glass substrate, and I represents a transmitted-light intensity, that is, the intensity of the above light having been transmitted through the sample. The term "average absorbance" refers to an average absorbance within the above wavelength range.

As illustrated in FIG. 6, the variation of the average absorbance with respect to a variation of the mass per unit area (hereinafter referred to as "per-unit-area-mass absorbance inclination") for a case where the sample is irradiated with light having a wavelength of not less than 390 nm and not more than 420 nm is greater than the per-unit-area-mass absorbance inclination for a case where the sample is irradiated with light having a wavelength of not less than 680 nm and not more than 700 nm. The per-unit-area-mass absorbance inclination for a case where the sample is irradiated with light having a wavelength within a range of not less than 700 nm (second wavelength) (for example, a wavelength within a range of not less than 700 nm and not more than 850 nm) is similar (not shown in FIG. 6) to the per-unit-area-mass absorbance inclination for a case where the sample is irradiated with light having a wavelength of not less than 680 nm and not more than 700 nm.

(Determining Mass Per Unit Area of Applied Layer)

The procedure below allows the mass per unit area of the heat-resistant layer 4 in the separator 12 to be determined on the basis of the relations illustrated in FIGS. 5 and 6.

(1) Determine the inclination (proportion coefficient) of the absorbance with respect to the mass per unit area from the results of measurement of the absorbance that each layer in the separator 12 (namely, the heat-resistant layer 4 and the base film 5) exhibits with respect to the above wavelengths. For this procedure, $X_4$ represents the proportion coefficient of the absorbance that the heat-resistant layer 4 exhibits with respect to a wavelength X; $Y_4$ represents the proportion coefficient of the absorbance that the heat-resistant layer 4 exhibits with respect to a wavelength Y; $X_5$ represents the proportion coefficient of absorbance that the base film 5 exhibits with respect to the wavelength X; and $Y_5$ represents the proportion coefficient of absorbance that the base film 5 exhibits with respect to the wavelength Y.

(2) Measure the absorbance $X_{total}$ of the separator 12 for a case where the separator 12 is irradiated with light having a wavelength of not less than 680 nm and not more than 700 nm.

(3) Measure the absorbance $Y_{total}$ of the separator 12 for a case where the separator 12 is irradiated with light having a wavelength of not less than 390 nm and not more than 420 nm.

(4) The following simultaneous equations hold:

$$X_4 W_4 + X_5 W_5 = X_{total}$$

$$Y_4 W_4 + Y_5 W_5 = Y_{total},$$

where $W_4$ represents the mass per unit area of the heat-resistant layer 4 in the separator 12, and $W_5$ represents the mass per unit area of the base film 5 in the separator 12. Calculate $W_4$ and $W_5$ from the above simultaneous equations.

The wavelength of light with which the separator 12 is irradiated can, even in a case where the applied layer is other than a heat-resistant layer containing aramid, be selected as appropriate from the ultraviolet to infrared regions depending on the material of the applied layer to determine the mass per unit area of the applied layer. Specifically, in a case where, for example, the applied layer contains PVDF, the above steps (1) to (4) can be carried out with use of light having a wave number of 790 to 840 cm$^{-1}$ (wavelength of 12700 nm to 11900 nm), which light is characteristically absorbed by PVDF, to determine the mass per unit area of the applied layer.

(Determining Mass Per Unit Area of Applied Layer for Case where Separator 12 Includes Three or More Layers)

In a case where the separator 12 includes three or more different layers, the proportion coefficient of absorbance of each layer can be calculated with use of the same number of kinds of light as the number of the layers to determine the mass per unit area of each layer. In a case where, for example, the separator 12 includes four different layers, the above simultaneous equations, which are simultaneous linear equations in four unknowns, can be solved to determine the mass per unit area of each layer.

Even in a case where the separator 12 includes an aramid-containing applied layer on a surface of the base film 5 and a ceramic-containing applied layer on another surface of the base film 5, the mass per unit area of each applied layer can be determined. Further, even in a case where the separator 12 includes an aramid-containing applied layer on a surface of the base film 5 and an adhesive layer on that surface of the base film 5 which is opposite to the aramid-containing applied layer, the mass per unit area of the applied layer and that of the adhesive layer can be determined.

Embodiments of the present invention are not limited to determining the mass per unit area of an applied layer in a separator. Some embodiments of the present invention can determine the mass per unit area of an applied layer in, for example, an optical film including (i) a base film such as a transparent film, a phase difference film, and a polarizing film and (ii) such an applied layer placed on the base film as an adhesive layer or a cured film of a liquid crystal compound.

«Configuration of Per-Unit-Area-Mass Measuring Device»

Figure 7:
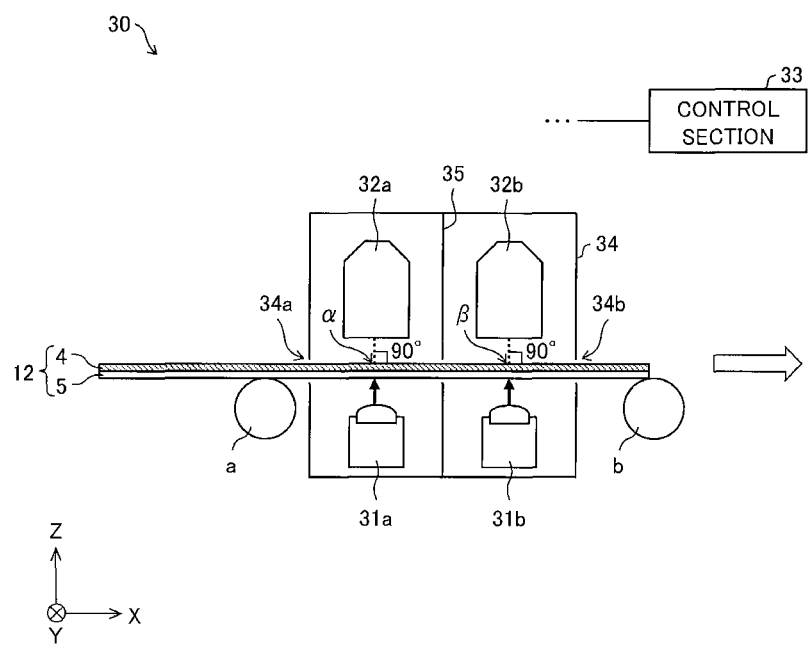
FIG. 7 is a side view of a per-unit-area-mass measuring device for use in an inspecting step related to the applied layer illustrated in FIG. 4.

FIG. 7 is a side view of the per-unit-area-mass measuring device 30 for use in the inspecting step illustrated in (b) of FIG. 4, the side view illustrating a configuration of the per-unit-area-mass measuring device 30. As illustrated in FIG. 7, the per-unit-area-mass measuring device 30 includes light projectors 31a and 31b, light receivers 32a and 32b, a control section 33 (calculating section), a cover 34, and a partition plate 35.

FIG. 7 shows X, Y, and Z axes, which correspond to those shown in any drawing other than FIG. 7. The description below assumes that the separator 12 is transferred in an X-axis forward direction with use of transfer rollers a and b and extends in a direction parallel with the XY plane.

(Light Projectors and Light Receivers)

The light projectors 31a and 31b each include (i) a light-emitting section including a plurality of light-emitting diodes (LEDs) arranged in the Y-axis direction and (ii) a diffusing plate configured to diffuse light emitted by the LEDs. The light projectors 31a and 31b each project light substantially over the entire width of the separator 12 in the Y-axis direction. The light projector 31a projects onto the separator 12 light (measurement light) having a center wavelength of 405 nm (first wavelength). The light projector 31b projects onto the separator 12 light (measurement light) having a center wavelength of 850 nm (second wavelength). The light projectors 31a and 31b are separated from the separator 12 by a distance of 1 mm to 20 mm.

The light receivers 32a and 32b each receive light substantially over the entire width of the separator 12 in the Y-axis direction. The light receiver 32a receives light projected by the light projector 31a and transmitted through the separator 12. The light receiver 32b receives light projected by the light projector 31b and transmitted through the separator 12. The light receivers 32a and 32b are separated from the separator 12 by a distance of 1 mm to 20 mm.

FIG. 7 shows a position α, which is a spatial position at which the measurement light that the light projector 31a projects and the light receiver 32a receives crosses the separator 12. FIG. 7 also shows a position β, which is a spatial position at which the measurement light that the light projector 31b projects and the light receiver 32b receives crosses the separator 12. That portion of the separator 12 which lies at the position α at a time point is moved to lie at the position β after a predetermined time period. This means that (i) the measurement light received by the light receiver 32a at a time point and (ii) the measurement light received by the light receiver 32b after the predetermined time period are transmitted through an identical portion of the separator 12.

(Control Section)

The control section 33 is connected to the light projectors 31a and 31b and the light receivers 32a and 32b, and is capable of controlling the respective operations of those members connected to the control section 33. The control section 33 is, for example, capable of controlling the respective operations of the light receivers 32a and 32b to allow for comparison between (i) the transmitted-light intensity of measurement light received by the light receiver 32a at a time point and (ii) the transmitted-light intensity of measurement light received by the light receiver 32b after the predetermined time period.

Specifically, the control section 33 includes a logic circuit (hardware) provided in an integrated circuit (IC chip) or the like. The control section 33 is, however, not limited to such a configuration, and may include software as executed by a central processing unit (CPU).

In the latter case, the control section 33 includes: a CPU that executes instructions of a program that is software realizing the foregoing functions; a read only memory (ROM) or a storage device (each referred to as "storage medium") storing the program and various kinds of data in such a form that they are readable by a computer (or a CPU); and a random access memory (RAM) that develops the program in executable form. The object of an embodiment of the present invention can be achieved by a computer (or a CPU) reading and executing the program stored in the storage medium. The storage medium may be "a non-transitory tangible medium" such as a tape, a disk, a card, a semiconductor memory, and a programmable logic circuit. Further, the program may be made available to the computer via any transmission medium (such as a communication network and a broadcast wave) which enables transmission of the program. An embodiment of the present invention may further be in the form of a data signal embedded in a carrier wave and embodied by electronic transmission of the programs.

(Cover and Partition Plate)

The cover 34 encases the light projectors 31a and 31b and the light receivers 32a and 32b to prevent entry of disturbance light. The cover 34 has (i) an opening 34a through which the separator 12 is transferred to the inside of the cover 34 and (ii) an opening 34b through which the separator 12 is transferred to the outside of the cover 34. The partition plate 35 prevents (i) light projected by the light projector 31a from entering the light receiver 32b and (ii) light projected by the light projector 31b from entering the light receiver 32a.

«Operation of Per-Unit-Area-Mass Measuring Device»

The per-unit-area-mass measuring device 30 operates as follows:

(1) The light projector 31b projects light having a center wavelength of 850 nm onto the separator 12. The light receiver 32b receives the light as transmitted through the separator 12. The control section 33 determines the absorbance −log(I/Iin), where Iin represents an incident light intensity, that is, the intensity of light emitted by the light projector 31a, and I represents a transmitted-light intensity, that is, the intensity of light received by the light receiver 32a.

(2) The light projector 31a projects light having a center wavelength of 405 nm onto the separator 12. The light receiver 32a receives the light as transmitted through the separator 12. The control section 33 determines the absorbance −log(I/Iin), where Iin represents an incident light intensity, that is, the intensity of light emitted by the light projector 31b, and I represents a transmitted-light intensity, that is, the intensity of light received by the light receiver 32b.

(3) The control section 33 converts each of the two absorbances into a mass per unit area for the heat-resistant layer 4 on the basis of the proportional relation between the absorbance and the mass per unit area.

«Effects of Per-Unit-Area-Mass Measuring Device»

The two kinds of light transmitted through the separator 12 in the above steps (1) and (2) (namely, a light-transmitting step and a light-measuring step) reflect the difference between (i) the wavelength range of light that the base film 5 absorbs and (ii) the wavelength range of light that the heat-resistant layer 4 absorbs. A greater unevenness in the thickness of the base film 5 results in a greater unevenness in the absorbance thereof. However, since the mass of the heat-resistant layer 4 per unit area is proportional to the absorbance of the heat-resistant layer 4, the above step (3) (namely, a calculating step) allows the mass per unit area to be determined.

The three steps above make it possible to measure the mass per unit area of the heat-resistant layer 4 in the separator 12 while preventing a measurement error from being caused by unevenness in the thickness of the base film 5 in the separator 12.

(Per-Unit-Area-Mass Measuring Method and Laminated Film Producing Method)

An embodiment of the present invention covers in its scope a per-unit-area-mass measuring method including the light-transmitting step, the light-measuring step, and the calculating step each described above.

An embodiment of the present invention further covers in its scope a layered-film producing method including the light-transmitting step, the light-measuring step, and the calculating step each described above as well as a coating step of controlling the mass per unit area of the applied layer (heat-resistant layer 4) on the basis of the mass per unit area calculated in the calculating step. The coating step refers to, for example, bar coating illustrated in (a) of FIG. 4. The coating step may alternatively be gravure coating or dip coating. The expression "controlling the mass per unit area" above means adjusting, on the basis of the mass per unit area calculated in the calculating step, the amount of the coating solution with which the base film 5 is to be coated.

The base film 5 can be coated by a publicly known method. In the case of bar coating, for example, widening the distance between the base film 5 and the coating member 25 illustrated in (a) of FIG. 4 increases the coating amount of the coating solution 21, whereas narrowing that distance decreases the coating amount. In the case of gravure coating, increasing the rate of rotation of the gravure roll with respect to the speed of transfer of the base film 5 increases the coating amount of the coating solution 21, whereas decreasing that rate of rotation decreases the coating amount. In the case of dip coating, increasing the speed of transfer of the base film 5 in the coating solution 21 increases the coating amount of the coating solution 21, whereas decreasing that speed of transfer decreases the coating amount.

An embodiment of the present invention further covers in its scope a layered-film producing method including the light-transmitting step, the light-measuring step, and the calculating step each described above as well as a removing step of, on the basis of the mass per unit area calculated in the calculating step, removing a portion of the separator 12 which portion has an abnormal mass per unit area. The removing step is configured to cut off for removal a portion of a slit separator 12 (slit separator) at which portion (per-unit-area-mass abnormal portion) the mass per unit area exceeds or falls below a preset threshold. The remaining portions, without the portions cut off, of slit separators may be joined with each other to be wound around another core.

(Planar Per-Unit-Area-Mass Measurement and Pinhole Inspection)

The per-unit-area-mass measuring method involving use of the per-unit-area-mass measuring device 30 includes, as illustrated in FIG. 7, a transfer step of transferring a separator 12 in the X-axis forward direction with use of the transfer rollers a and b. The light-transmitting step described above causes two kinds of measurement light (namely, light that the light projector 31a projects and light that the light projector 31b projects) to be transmitted through the separator 12 which measurement light is in the shape of a line extending over a surface of the separator 12 along the Y-axis direction, which crosses the X-axis direction. The light-measuring step described above allows for measurement of a transmitted-light intensity in regions corresponding respectively to the two kinds of linear measurement light. This allows the mass per unit area to be measured over a range in the shape of not a dot or a line but a plane.

The per-unit-area-mass measuring device 30 is also capable of measuring the mass of the heat-resistant layer 4 per unit area over the entire surface of the separator 12. In a case where the separator 12 has a pinhole, the transmitted-light intensity has distinct contrast at the pinhole. In view of that, the per-unit-area-mass measuring device 30 is further capable of inspecting the separator 12 for any pinhole while measuring the mass per unit area. The per-unit-area-mass measuring device 30 can be, in other words, a combined device that integrates a per-unit-area-mass measuring device with a defect inspector.

Further, the per-unit-area-mass measuring device 30 is capable of detecting an end of the separator 12 (continuous monitoring) by measuring the mass per unit area over the entire surface of the separator 12. The per-unit-area-mass measuring device 30 is thus capable of identifying defect coordinates, which indicate the position at which a defect such as a pinhole is present (for example, the length extending from an end of the separator 12 to the position at which a defect is present).

The inspecting step is followed by a slitting step, for which defect coordinates have preferably been identified. However, during the inspecting step, the separator 12 may meander randomly, which has made it difficult for conventional inspection devices to identify defect coordinates. Since the per-unit-area-mass measuring device 30 is capable of identifying defect coordinates, those defect coordinates can be utilized during the slitting step for an increased yield of slit separators.

(Accuracy of Measurement)

The per-unit-area-mass measuring device 30 is capable of measuring the mass per unit area with an accuracy of 0.1 $g/m^2$. For an increased accuracy, the light projectors 31a and 31b should each preferably be capable of projecting light having a single wavelength.

(Measurement Method)

The per-unit-area-mass measuring device 30 is a transmissive per-unit-area-mass measuring device: It causes measurement light to be transmitted through a separator 12. For an increased amount of measurement light transmitted, a straight line connecting a light projector and a light receiver should form, with a separator 12, an angle of preferably not less than 80 degrees and not more than 100 degrees, more preferably not less than 85 degrees and not more than 95 degrees. A reflective per-unit-area-mass measuring device, which causes measurement light to be reflected by the separator 12, may not be able to observe a variation in the intensity of reflected measurement light as a variation in the mass per unit area of a heat-resistant layer 4 in the separator 12, with the result of a failure to measure the mass per unit area. The per-unit-area-mass measuring device 30 is capable of measuring the mass per unit area of an applied layer in even a separator of which a reflective per-unit-area-mass measuring device is incapable of measurement.

«Other Configuration»

(Calibration)

Figure 8:
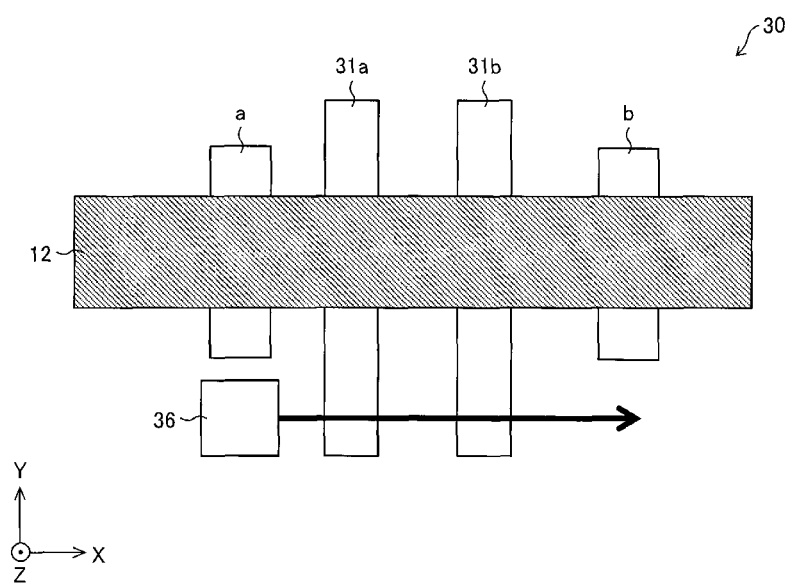
FIG. 8 is a plan view of the per-unit-area-mass measuring device illustrated in FIG. 7, the plan view illustrating a configuration of the per-unit-area-mass measuring device.

FIG. 8 is a plan view of the per-unit-area-mass measuring device 30 illustrated in FIG. 7, the plan view illustrating a configuration of the per-unit-area-mass measuring device 30. FIG. 8 omits the light receivers 32a and 32b, the control section 33, the cover 34, and the partition plate 35. The per-unit-area-mass measuring device 30, as illustrated in FIG. 8, further includes a sample holder 36. The sample holder 36 holds a sample with a known absorbance. The sample holder 36 moves in the X-axis direction at a transfer speed equivalent to that during production of the separator 12. Measurement light is transmitted through the sample held by the sample holder 36 for measurement of the absorbance. This makes it possible to learn the correct proportional relation between the absorbance and the mass per unit area which proportional relation is utilized for the conversion of an absorbance into a mass per unit area.

(Light Receivers)

Figure 9:
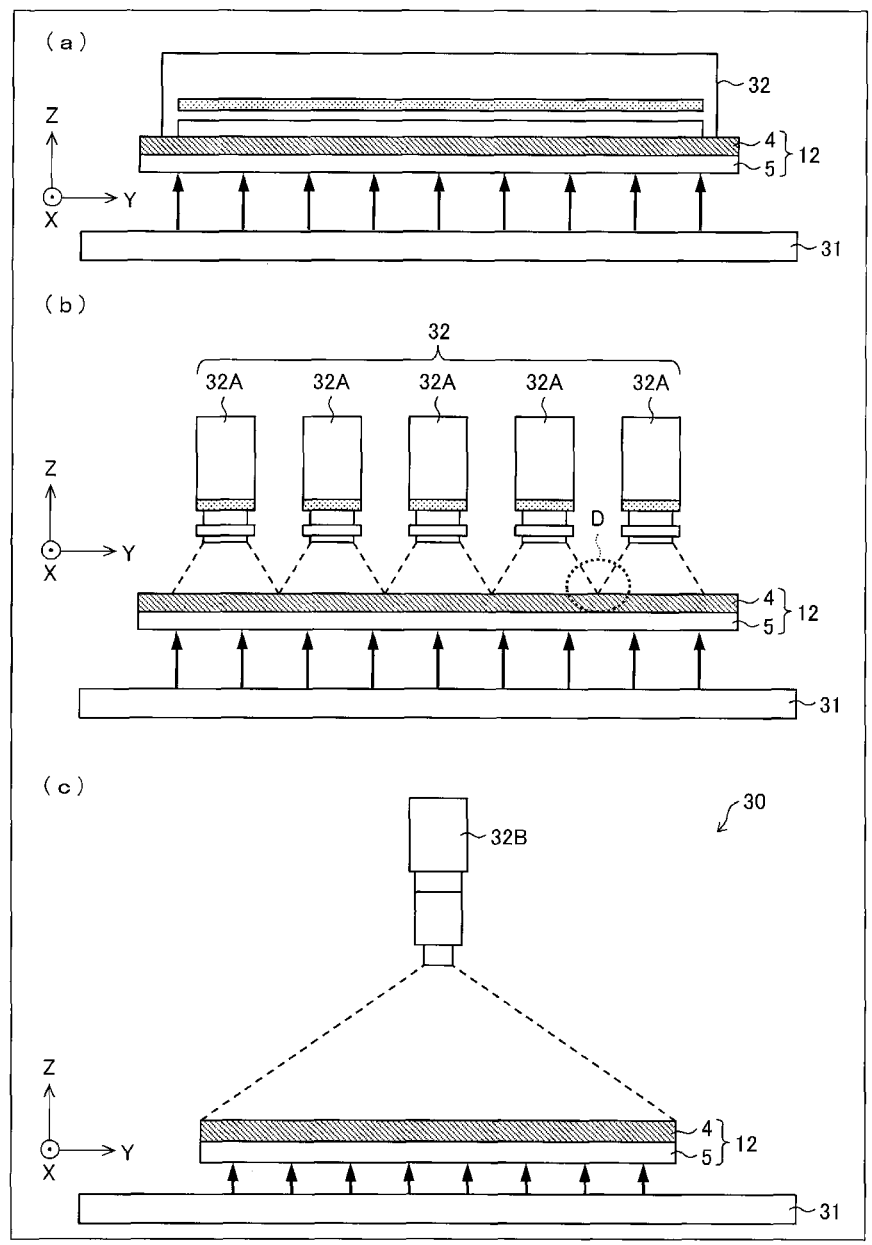
FIG. 9 provides elevational views of a light receiver for the per-unit-area-mass measuring device illustrated in FIG. 7, the elevational views each illustrating a configuration of the light receiver.

FIG. 9 provides elevational views of a light receiver 32 for the per-unit-area-mass measuring device 30 illustrated in FIG. 7, the elevational views each illustrating a configuration of the light receiver 32. (a) of FIG. 9 illustrates a configuration of the light receiver 32 for a case where the light receiver 32 is a contact image sensor (CIS) module. (b) of FIG. 9 illustrates a configuration of the light receiver 32 for a case where the light receiver 32 includes a plurality of charge coupled device (CCD) cameras 32A. (c) of FIG. 9 illustrates a configuration of the light receiver 32 for a case where the light receiver 32 is a wide-angle CCD camera 32B. The light receivers 32a and 32b are collectively assigned the reference numeral "32" as the respective configurations of the light receivers 32a and 32b appear identical to each other in the elevational views. Similarly, the light projectors 31a and 31b are collectively assigned the reference numeral "31".

The light receiver 32 is, as illustrated in (a) of FIG. 9, a CIS module including a plurality of image sensing elements and a lens array each arranged in the Y-axis direction and configured to receive light from substantially the entire width of the separator 12 in the Y-axis direction. The light receiver 32 is, however, not limited to such a configuration. The light receiver 32 may, as illustrated in (b) of FIG. 9, include a plurality of CCD cameras 32A (light receivers). Alternatively, the light receiver 32 may, as illustrated in (c) of FIG. 9, include a wide-angle CCD camera 32B (light receiver).

(CIS Module)

A CIS module has the characteristics listed below.

Individual modules have only small unevenness in quality. No additional configuration is necessary for prevention of an adverse effect arising from quality unevenness.

Distortion of a field of view (for example, distortion occurring in the field of view D in (b) of FIG. 9) is small as compared with a configuration involving use of a lens having a large diameter. This characteristic eliminates the need for optical correction (for example, for aberration or light amount ratio).

Chromatic aberration is small as compared with a configuration involving use of a lens having a large diameter. This characteristic makes it possible to reliably receive light on the ultraviolet (UV) side (for example, light having a center wavelength of 405 nm) and light on the near-infrared (NIR) side (for example, light having a center wavelength of 850 nm).

The resolution is 80 μm. Another resolution can be selected.

The field of view is 1150 mm. In a case where the separator 12 has a width of approximately 1000 mm, using a single CIS module as a single light receiver allows for measurement of the mass of the heat-resistant layer 4 per unit area over the entire width of the separator 12. Another field of view can be selected.

Calibration (including diagnosis of degradation of the per-unit-area-mass measuring device 30 over time) and per-unit-area-mass measurement for determining a formula for conversion into a mass per unit area can simply be carried out at a single position at a widthwise end of the separator 12.

The machine construction has a single axle.

(CCD Camera)

A CCD camera has the characteristics listed below.

Costs are low as compared with a CIS module.

The number of options (field of view, resolution) is large as compared with a CIS module.

The resolution is 60 μm. Another resolution can be selected.

The field of view is 200 mm. In a case where the separator 12 has a width of approximately 1000 mm, using six CCD cameras as a single light receiver allows for reliable measurement of the mass of the heat-resistant layer 4 per unit area over the entire width of the separator 12. Another field of view can be selected.

Optical correction is necessary of distortion of a field of view (for example, distortion occurring in the field of view D in (b) of FIG. 9).

Chromatic aberration is large as compared with a CIS module.

Calibration and per-unit-area-mass measurement for determining a formula for conversion into a mass per unit area need to be carried out for each CCD camera.

The machine construction has a double axle, and is more complex than that of a CIS module.

(Wide-Angle CCD Camera)

A wide-angle CCD camera has the characteristics listed below.

Costs are low as compared with a CIS module or a configuration of a plurality of CCD cameras arranged in the Y-axis direction.

The number of options (field of view, resolution) is large as compared with a CIS module.

Optical correction is necessary of distortion of a field of view.

The distortion of a field of view is large as compared with a configuration of a plurality of CCD cameras arranged in the Y-axis direction.

Chromatic aberration is large as compared with a CIS module.

(Traverse Measurement)

Figure 10:
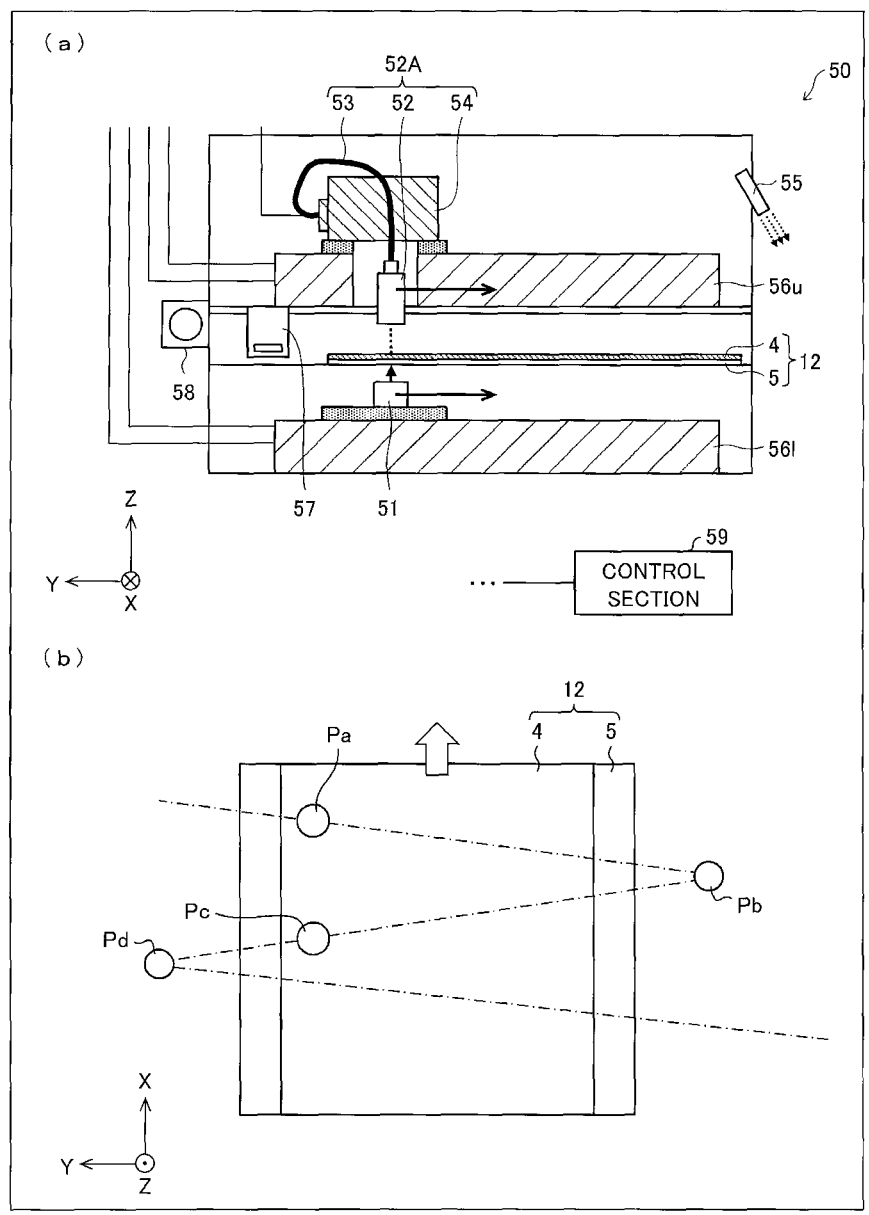
FIG. 10 provides an elevational view and a plan view of a per-unit-area-mass measuring device configured to carry out traverse measurement, the views each illustrating a configuration of the per-unit-area-mass measuring device.

FIG. 10 provides views of a per-unit-area-mass measuring device 50 configured to carry out traverse measurement, the views each illustrating a configuration of the per-unit-area-mass measuring device 50. (a) of FIG. 10 is an elevational view of the per-unit-area-mass measuring device 50. (b) of FIG. 10 is a plan view of the per-unit-area-mass measuring device 50. The term "traverse measurement" refers to per-unit-area-mass measurement carried out while a measurement position is moved. The per-unit-area-mass measuring device 50, as illustrated in (a) of FIG. 10, includes a light projector 51, a spectrometer section 52A, traverse units 56u and 56l, a sample holder 57, and a control section 59 (calculating section). The per-unit-area-mass measuring device 50 may further include a blower 55 and an emergency stop button 58.

The light projector 51 is a light source (for example, an LED) configured to emit measurement light including light having a wavelength of 405 nm (first wavelength) and light having a wavelength of 850 nm (second wavelength). The measurement light is, however, not limited to such light. The measurement light may include light having a wavelength of not less than 390 nm and not more than 420 nm (first wavelength) and light having a wavelength of not less than 680 nm and not more than 850 nm (second wavelength).

The spectrometer section 52A includes a light receiver 52, a light-receiving fiber 53, and a spectrometer 54. The light receiver 52 is a tube-shaped member including a lens, and receives light projected by the light projector 51 and transmitted through the separator 12. The light-receiving fiber 53 guides light received by the light receiver 52 to the spectrometer 54. The spectrometer 54 separates light guided through the light-receiving fiber 53 into different spectral components, and measures the respective transmitted-light intensities at the first and second wavelengths, which are different from each other. The control section 59 determines the absorbance for each of the transmitted-light intensities, and converts each of the two absorbances into a mass per unit area for the heat-resistant layer 4.

The traverse unit 56u reciprocates the light receiver 52 in the Y-axis direction at a predetermined speed. The light-receiving fiber 53 is long enough to guide light from the light receiver 52 to the spectrometer 54 even in a case where the light receiver 52 is moved. The traverse unit 56l reciprocates the light projector 51 in the Y-axis direction at a predetermined speed. The traverse unit 56u and the traverse unit 56l are moved together. This configuration allows the light projector 51 and the light receiver 52 to be reciprocated in synchronization with each other so that light projected by the light projector 51 enters the light receiver 52. In other words, measurement light emitted by the reciprocating light projector 51 (reciprocating position) is transmitted through the separator 12 and is received by the light receiver 52 reciprocating in synchronization with the light projector 51 (region corresponding to the reciprocating position).

The light projector 51 and the light receiver 52 are calibrated with the sample holder 57 holding a sample with a known absorbance. During the calibration, the traverse unit 56u moves the light receiver 52 to the position of the sample holder 57. The traverse unit 56l also moves the light projector 51 to the position of the sample holder 57. Pressing down the emergency stop button 58 stops the respective operations of the traverse units 56u and 56l.

The traverse units 56u and 56l slow down at a position beyond the film width for a turn. The blower 55 may be disposed at that position to prevent deposition of dust on devices connected to the traverse unit 56l. The blower 55 is equipped with an air pipe connected thereto, and blows air from the air pipe toward a position on the separator 12 onto which position the light projector 51 is projecting light.

The control section 59 is connected to the light projector 51, the spectrometer 54, the blower 55, the traverse units 56u and 56l, and the emergency stop button 58, and controls the respective operations of those members connected to the control section 59. The control section 59 has a specific configuration similar to that of the control section 33 described above.

While the separator 12 is being transferred in the X-axis forward direction (single direction), the per-unit-area-mass measurement position of the per-unit-area-mass measuring device 50, as illustrated in (b) of FIG. 10, moves over the separator 12 sequentially from a position Pa to a position Pb, to a position Pc, and to a position Pd. The per-unit-area-mass measurement position is, as described above, in the form of a line that extends in the direction of the transfer of the separator 12 while reciprocating in the width direction of the separator 12.

The per-unit-area-mass measuring device 50 does not measure the mass of the heat-resistant layer 4 per unit area for a region between the positions Pa and Pc of the separator 12. Since the per-unit-area-mass measurement position is moved over the separator 12 in the pattern of the dotted-and-dashed line shown in (b) of FIG. 10, there is a region over the separator 12 for which region the mass per unit area is not measured as mentioned above.

(Measurement Involving Use of Plurality of Spectrometer Sections)

Figure 11:
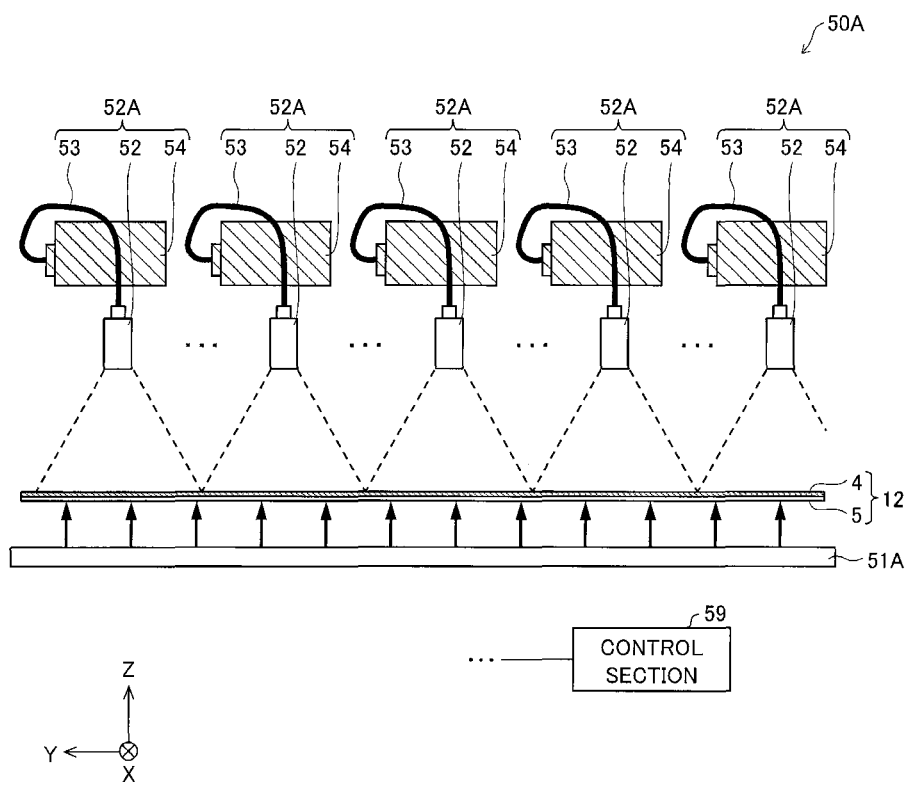
FIG. 11 is an elevational view of a per-unit-area-mass measuring device including a plurality of spectrometer sections, the elevational view illustrating a configuration of the per-unit-area-mass measuring device.

FIG. 11 is an elevational view of a per-unit-area-mass measuring device 50A including a plurality of spectrometer sections 52A, the elevational view illustrating a configuration of the per-unit-area-mass measuring device 50A. The per-unit-area-mass measuring device 50A, as illustrated in FIG. 11, includes a light projector 51A, five spectrometer sections 52A, and a control section 59 (calculating section).

The light projector 51A projects linear measurement light including light having a wavelength of not less than 390 nm and not more than 420 nm (first wavelength) and light having a wavelength of not less than 680 nm and not more than 850 nm (second wavelength) substantially over the entire width of the separator 12 in the Y-axis direction. The five spectrometer sections 52A are each configured such that (i) the light receiver 52 receives light, (ii) the light-receiving fiber 53 guides the light, and (iii) the spectrometer 54 separates the light into different spectral components and measures the respective transmitted-light intensities at the first and second wavelengths, which are different from each other.

The number of spectrometer sections 52A is not limited to five, and may be increased or decreased so as to be capable of separating measurement light emitted by the light projector 51A into different spectral components in a desired region of the separator 12. The light receivers 52 may each include an optical system configured to collect measurement light.

The control section 59 is connected to the light projector 51A and the respective spectrometers 54 of the five spectrometer sections 52A, and controls the respective operations of those members connected to the control section 59. The control section 59 determines the absorbance for each of the transmitted-light intensities, and converts each of the two absorbances into a mass per unit area for the heat-resistant layer 4.

(Traverse Measurement Involving No Use of Spectrometer Section)

Figure 12:
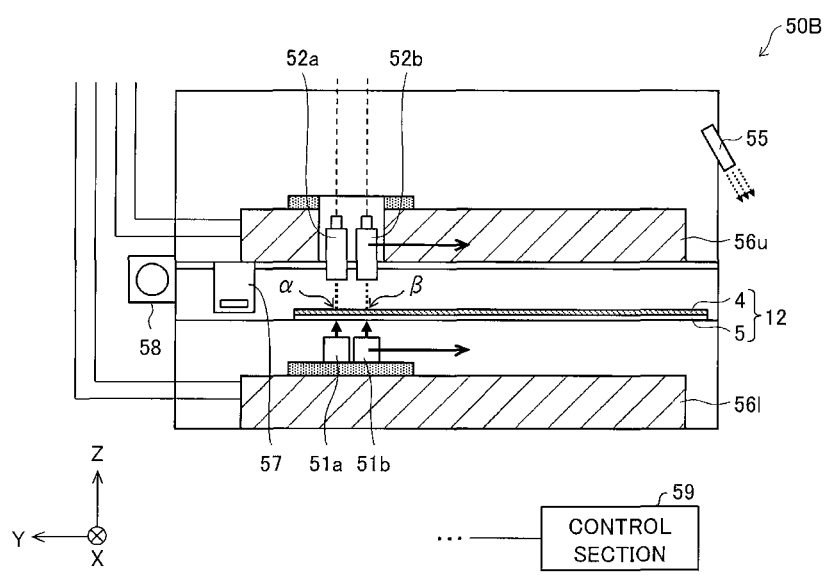
FIG. 12 is an elevational view of a per-unit-area-mass measuring device configured to carry out traverse measurement without use of a spectrometer section, the elevational view illustrating a configuration of the per-unit-area-mass measuring device.

FIG. 12 is an elevational view of a per-unit-area-mass measuring device 50B configured to carry out traverse measurement without use of a spectrometer section, the elevational view illustrating a configuration of the per-unit-area-mass measuring device 50B. The per-unit-area-mass measuring device 50B, as illustrated in FIG. 12, includes light projectors 51a and 51b, light receivers 52a and 52b, traverse units 56u and 56l, a sample holder 57, and a control section 59 (calculating section). The per-unit-area-mass measuring device 50B may further include a blower 55 and an emergency stop button 58.

The light projector 51a projects measurement light having a center wavelength of not less than 390 nm and not more than 420 nm (first wavelength). The light receiver 52a measures the transmitted-light intensity of the measurement light as transmitted through the separator 12. The light projector 51b projects measurement light having a center wavelength of not less than 680 nm and not more than 850 nm (second wavelength). The light receiver 52b measures the transmitted-light intensity of the measurement light as transmitted through the separator 12.

FIG. 12 shows a position α, which is a spatial position at which the measurement light that the light projector 51a projects and the light receiver 52a receives crosses the separator 12. FIG. 12 also shows a position β, which is a spatial position at which the measurement light that the light projector 51b projects and the light receiver 52b receives crosses the separator 12. In a case where unevenness in the thickness of the base film 5 in the separator 12 is negligibly small between the positions α and β, the light projectors 51*a* and 51*b* may be regarded as projecting measurement light onto an identical portion of the separator 12. The light projectors 51*a* and 51*b* and the light receivers 52*a* and 52*b* may be so arranged and angled that the two kinds of measurement light are projected onto an identical portion of the separator 12.

The control section 59 is connected to the light projectors 51*a* and 51*b* and the light receivers 52*a* and 52*b*, and controls the respective operations of those members connected to the control section 59. The control section 59 determines the absorbance for each of the transmitted-light intensities, and converts each of the two absorbances into a mass per unit area for the heat-resistant layer 4.

[Recap]

The per-unit-area-mass measurements described above can be classified as below on the basis of whether to separate measurement light and whether to move the position of emission of measurement light.

(Per-Unit-Area-Mass Measurement in which Measurement Light is Separated and the Position of Emission of Measurement Light is Moved)

The per-unit-area-mass measuring device 50 illustrated in (a) of FIG. 10 uses a per-unit-area-mass measuring method including: a light-transmitting step of causing measurement light to be transmitted through a separator 12; a light-measuring step of (i) separating, into a first beam having a first wavelength and a second beam having a second wavelength different from the first wavelength, the measurement light having been transmitted through the separator 12 and (ii) measuring respective transmitted-light intensities of the first and second beams; and a calculating step of calculating the mass per unit area of the heat-resistant layer 4 on a basis of the transmitted-light intensities. This per-unit-area-mass measuring method further includes: a transfer step of transferring the separator 12 in the X-axis forward direction during the light-transmitting step and the light-measuring step, wherein: in the light-transmitting step, the measurement light is emitted from a position that reciprocates in a direction crossing the Y-axis direction; and in the light-measuring step, the transmitted-light intensities are measured in a region corresponding to the reciprocating position.

With the above configuration, the per-unit-area-mass measurement range is, as illustrated in (b) of FIG. 10, in the shape of a line that extends in the direction of the transfer of the separator 12 while reciprocating in the width direction of the separator 12. This per-unit-area-mass measurement produces results that reflect a variation of the mass per unit area of the separator 12 which variation occurs in the direction in which the separator 12 is transferred. This makes it possible to carry out a coating step of controlling the mass per unit area of the heat-resistant layer 4 on the basis of the mass per unit area which mass has been calculated by the per-unit-area-mass measuring device 50 in the calculating step.

(Per-Unit-Area-Mass Measurement in which Measurement Light is Separated and the Position of Emission of Measurement Light is not Moved)

The per-unit-area-mass measuring device 50A illustrated in FIG. 11 uses a per-unit-area-mass measuring method including: a light-transmitting step of causing measurement light to be transmitted through a separator 12; a light-measuring step of (i) separating, into a first beam having a first wavelength and a second beam having a second wavelength different from the first wavelength, the measurement light having been transmitted through the separator 12 and (ii) measuring respective transmitted-light intensities of the first and second beams; and a calculating step of calculating the mass per unit area of the heat-resistant layer 4 on a basis of the transmitted-light intensities. This per-unit-area-mass measuring method further includes: a transfer step of transferring the separator in the X-axis forward direction during the light-transmitting step and the light-measuring step, wherein: in the light-transmitting step, the measurement light is in the shape of a line extending along Y-axis direction; and in the light-measuring step, the transmitted-light intensities are measured in a region corresponding to the shape of the measurement light.

The above configuration allows the mass per unit area to be measured over a range in the shape of a plane. This per-unit-area-mass measurement produces results that reflect a variation of the mass per unit area of the separator 12 which variation occurs in the direction in which the separator 12 is transferred. This makes it possible to carry out a coating step of controlling the mass per unit area of the heat-resistant layer 4 on the basis of the mass per unit area which mass has been calculated by the per-unit-area-mass measuring device 30 in the calculating step.

Measuring the mass per unit area over the entire surface of the separator 12 allows the mass per unit area to be measured thoroughly. The mass per unit area varies between a significant value and zero at an end of the separator 12. Further, the mass per unit area varies sharply at the position of a defect in the separator 12 (for example, a pinhole). This makes it possible to carry out a detecting step of detecting at least one of an end of the separator 12 and a defect on the basis of the transmitted-light intensities.

(Per-Unit-Area-Mass Measurement in which Measurement Light is not Separated and the Position of Emission of Measurement Light is Moved)

The per-unit-area-mass measuring device 50B illustrated in FIG. 12 uses a per-unit-area-mass measuring method including: a light-transmitting step of causing measurement light to be transmitted through a separator 12, the measurement light including a first beam having a center wavelength at a first wavelength and a second beam having a center wavelength at a second wavelength different from the first wavelength; a light-measuring step of measuring respective transmitted-light intensities of the first and second beams of the measurement light having been transmitted through the separator 12; and a calculating step of calculating the mass per unit area of the heat-resistant layer 4 on the basis of the transmitted-light intensities. This per-unit-area-mass measuring method further includes: a transfer step of transferring the separator 12 in the X-axis forward direction during the light-transmitting step and the light-measuring step, wherein: in the light-transmitting step, the measurement light is emitted from a position that reciprocates in a direction crossing the Y-axis direction; and in the light-measuring step, the transmitted-light intensities are measured in a region corresponding to the reciprocating position.

With the above configuration, the per-unit-area-mass measurement range is in the shape of a line that reciprocates obliquely in the width direction of the separator 12 to move in the direction in which the separator 12 is transferred. This makes it possible to, as described above, carry out a coating step of controlling the mass per unit area of the heat-resistant layer 4 on the basis of the mass per unit area which mass has been calculated by the per-unit-area-mass measuring device 50 in the calculating step.

(Per-Unit-Area-Mass Measurement in which Measurement Light is not Separated and the Position of Emission of Measurement Light is not Moved)

The per-unit-area-mass measuring device 30 illustrated in FIG. 7 uses a per-unit-area-mass measuring method including: a light-transmitting step of causing measurement light to be transmitted through a separator 12, the measurement light including a first beam having a center wavelength at a first wavelength and a second beam having a center wavelength at a second wavelength different from the first wavelength; a light-measuring step of measuring respective transmitted-light intensities of the first and second beams of the measurement light having been transmitted through the separator 12; and a calculating step of calculating the mass per unit area of the heat-resistant layer 4 on the basis of the transmitted-light intensities. This per-unit-area-mass measuring method further includes: a transfer step of transferring the separator 12 in the X-axis forward direction during the light-transmitting step and the light-measuring step, wherein: in the light-transmitting step, the measurement light is in the shape of a line extending along Y-axis direction; and in the light-measuring step, the transmitted-light intensities are measured in a region corresponding to the shape of the measurement light.

The above configuration allows the mass per unit area to be measured over a range in the shape of a plane. This makes it possible to, as described above, carry out a coating step of controlling the mass per unit area of the heat-resistant layer 4 on the basis of the mass per unit area which mass has been calculated by the per-unit-area-mass measuring device 30 in the calculating step.

Measuring the mass per unit area over the entire surface of the separator 12 allows the mass per unit area to be measured thoroughly. This makes it possible to, as described above, carry out a detecting step of detecting at least one of an end of the separator 12 and a defect on the basis of the transmitted-light intensities.

[Other]

A method of an embodiment of the present invention for measuring a mass per unit area is a method for measuring a mass per unit area of an applied layer in a layered film including a base film and the applied layer provided on the base film, the method including: a light-transmitting step of causing measurement light to be transmitted through the layered film, the measurement light including a first beam having a center wavelength at a first wavelength and a second beam having a center wavelength at a second wavelength different from the first wavelength; a light-measuring step of measuring respective transmitted-light intensities of the first and second beams of the measurement light having been transmitted through the layered film; and a calculating step of calculating the mass per unit area of the applied layer on a basis of the transmitted-light intensities.

In the above method, the transmitted-light intensity as the intensity of measurement light that is transmitted through the layered film depends on the mass per unit area of the applied layer and the mass per unit area of the base film.

In view of that, by (i) measuring in advance the absorbance of each of the applied layer and the base film for each of a first beam of measurement light which first beam has a center wavelength at a first wavelength (hereinafter referred to as "first measurement light") and a second beam of the measurement light which second beam has a center wavelength at a second wavelength (hereinafter referred to as "select measurement light") and (ii) determining the inclination (proportion coefficient) of the absorbance with respect to the mass per unit area, it is possible to calculate the mass per unit area of the applied layer from (i) the proportion coefficient, determined in advance, of each of the applied layer and the base film with respect to each wavelength and (ii) the transmitted-light intensity measured of the layered film with respect to each beam of the measurement light.

Since two beams of the measurement light are transmitted through the same portion of the layered film, it is possible to measure the mass per unit area of an applied layer in a layered film while preventing a measurement error such as the above from being caused by unevenness in the thickness of a base film in the layered film.

Further, a method of an embodiment of the present invention for measuring a mass per unit area is a method for measuring a mass per unit area of an applied layer in a layered film including a base film and the applied layer provided on the base film, the method including: a light-transmitting step of causing measurement light to be transmitted through the layered film; a light-measuring step of (i) separating, into a first beam having a first wavelength and a second beam having a second wavelength different from the first wavelength, the measurement light having been transmitted through the layered film and (ii) measuring respective transmitted-light intensities of the first and second beams; and a calculating step of calculating the mass per unit area of the applied layer on a basis of the transmitted-light intensities.

With the above method, the transmitted-light intensity as the intensity measured through separation of measurement light that is transmitted through the layered film depends on the mass per unit area of the applied layer and the mass per unit area of the base film.

In view of that, by (i) measuring in advance the absorbance of each of the applied layer and the base film for each of the first wavelength and the second wavelength and (ii) determining the inclination (proportion coefficient) of the absorbance with respect to the mass per unit area, it is possible to calculate the mass per unit area of the applied layer from (i) the proportion coefficient, determined in advance, of each of the applied layer and the base film with respect to each wavelength and (ii) the transmitted-light intensity measured of the layered film with respect to each wavelength.

Since the respective transmitted-light intensities of the first and second wavelengths are measured through separation of the same measurement light having been transmitted through the layered film, it is possible to measure the mass per unit area of an applied layer in a layered film while preventing a measurement error such as the above from being caused by unevenness in the thickness of a base film in the layered film.

The method of an embodiment of the present invention may further include: a transfer step of transferring the layered film in a single direction during the light-transmitting step and the light-measuring step, wherein: in the light-transmitting step, the measurement light is emitted from a position over a surface of the layered film which position reciprocates in a direction crossing the single direction; and in the light-measuring step, the transmitted-light intensities are measured in a region corresponding to the reciprocating position.

With the above method, the per-unit-area-mass measurement range is in the shape of a line that reciprocates obliquely in the width direction of the layered film to move in the direction in which the layered film is transferred.

The method of an embodiment of the present invention may further include: a transfer step of transferring the layered film in a single direction during the light-transmitting step and the light-measuring step, wherein: in the light-transmitting step, the measurement light is in a shape of a line extending over a surface of the layered film along a direction crossing the single direction; and in the light-measuring step, the transmitted-light intensities are measured in a region corresponding to the shape of the measurement light.

The above method allows the mass per unit area to be measured over a range in the shape of not a dot or a line but a plane.

The method of an embodiment of the present invention may be arranged such that the measurement light and the layered film form an angle of not less than 80° and not more than 100'.

The above method allows more measurement light to be transmitted through the layered film.

The method of an embodiment of the present invention may be arranged such that the applied layer is an aramid layer containing aramid, the first wavelength is within a range of not less than 390 nm and not more than 420 nm; and the second wavelength is within a range of not less than 680 nm and not more than 700 nm.

With the above method, aramid tends to absorb measurement light having a first wavelength and not to absorb measurement light having a second wavelength. This allows the mass per unit area of the aramid layer to be measured more accurately.

The method of an embodiment of the present invention may be arranged such that the applied layer is an aramid layer containing aramid, the first wavelength is within a range of not less than 390 nm and not more than 420 nm; and the second wavelength is within a range of not less than 700 nm and not more than 850 nm.

The mass per unit area of an applied layer in a layered film is typically measured in an environment where visible light enters the layered film. Visible light does not contain a large amount of a component having wavelengths within the range of not less than 700 nm and not more than 850 nm. The above method allows the measurement to be less influenced by visible light as disturbance light, and thus allows the mass per unit area of the aramid layer to be measured more accurately.

The method of an embodiment of the present invention may further include: a detecting step of detecting at least one of an end of the layered film and a defect on the basis of the transmitted-light intensities.

The above method makes it possible to detect an end of the layered film and a defect while measuring the mass per unit area of the applied layer.

A method of an embodiment of the present invention for producing a layered film is a method for producing a layered film including a base film and an applied layer on the base film, the method including: each step included in any method above; and a coating step of controlling the mass per unit area of the applied layer on a basis of the mass per unit area which mass has been calculated in the calculating step.

The above method makes it possible to produce a layered film including an applied layer having a more uniform mass per unit area.

A method of an embodiment of the present invention for producing a layered film is a method for producing a layered film including a base film and an applied layer on the base film, the method including: each step included in any method above; and a removing step of removing a per-unit-area-mass abnormal portion of the layered film on a basis of the mass per unit area which mass has been calculated in the calculating step.

The above method makes it possible to remove a per-unit-area-mass abnormal portion on the basis of a planar measurement range, and thus improves the yield of a layered film.

A device of an embodiment of the present invention for measuring a mass per unit area is a device for measuring a mass per unit area of an applied layer in a layered film including a base film and the applied layer provided on the base film, the device including: two light projectors, a first one of the two light projectors being configured to project a first beam of measurement light which first beam has a center wavelength at a first wavelength, a second one of the two light projectors being configured to project a second beam of the measurement light which second beam has a center wavelength at a second wavelength different from the first wavelength; two light receivers, a first one of the two light receivers being configured to measure a transmitted-light intensity of the first beam of the measurement light having been transmitted through the layered film, a second one of the two light receivers being configured to measure a transmitted-light intensity of the second beam of the measurement light having been transmitted through the layered film; and a calculating section configured to calculate the mass per unit area of the applied layer on a basis of the transmitted-light intensities.

A device of an embodiment of the present invention for measuring a mass per unit area is a device for measuring a mass per unit area of an applied layer in a layered film including a base film and the applied layer provided on the base film, the device including: a light projector configured to project measurement light; a spectrometer section configured to (i) separate, into a first beam having a first wavelength and a second beam having a second wavelength different from the first wavelength, the measurement light having been transmitted through the layered film and (ii) measure respective transmitted-light intensities of the first and second beams; and a calculating section configured to calculate the mass per unit area of the applied layer on a basis of the transmitted-light intensities.

[Supplemental Notes]

The present invention is not limited to the embodiments, but can be altered by a skilled person in the art within the scope of the claims. The present invention also encompasses, in its technical scope, any embodiment derived by combining technical means disclosed in differing embodiments.

INDUSTRIAL APPLICABILITY

An embodiment of the present invention is applicable also to measurement of the mass per unit area of an applied layer in a light-transmitting film other than a layered film.

REFERENCE SIGNS LIST

1 Lithium-ion secondary battery
4 Heat-resistant layer
5 Base film
21 Coating solution
25 Coating member
30 Per-unit-area-mass measuring device
31, 31a, 31b Light projector
32, 32a, 32b Light receiver
32A, 32B CCD camera (light receiver)

33 Control section (calculating section)
50 Per-unit-area-mass measuring device
51 Light projector
52A Spectrometer section
59 Control section (calculating section)

The invention claimed is:

1. A method for measuring a mass per unit area of an applied layer in a layered film including a base film and the applied layer provided on the base film, the method comprising:
a light-transmitting step of causing measurement light to be transmitted through the layered film, the measurement light including a first beam having a center wavelength at a first wavelength and a second beam having a center wavelength at a second wavelength different from the first wavelength;
a light-measuring step of measuring respective transmitted-light intensities of the first and second beams of the measurement light having been transmitted through the layered film; and
a calculating step of calculating the mass per unit area of the applied layer on a basis of the transmitted-light intensities.

2. The method according to claim 1, further comprising:
a transfer step of transferring the layered film in a single direction during the light-transmitting step and the light-measuring step,
wherein:
in the light-transmitting step, the measurement light is emitted from a position over a surface of the layered film which position reciprocates in a direction crossing the single direction; and
in the light-measuring step, the transmitted-light intensities are measured in a region corresponding to the reciprocating position.

3. The method according to claim 1, further comprising:
a transfer step of transferring the layered film in a single direction during the light-transmitting step and the light-measuring step,
wherein:
in the light-transmitting step, the measurement light is in a shape of a line extending over a surface of the layered film along a direction crossing the single direction; and
in the light-measuring step, the transmitted-light intensities are measured in a region corresponding to the shape of the measurement light.

4. The method according to claim 1,
wherein
the measurement light and the layered film form an angle of not less than 80° and not more than 100°.

5. The method according to claim 1,
wherein:
the applied layer is an aramid layer containing aramid;
the first wavelength is within a range of not less than 390 nm and not more than 420 nm; and
the second wavelength is within a range of not less than 680 nm and not more than 700 nm.

6. The method according to claim 1,
wherein:
the applied layer is an aramid layer containing aramid;
the first wavelength is within a range of not less than 390 nm and not more than 420 nm; and
the second wavelength is within a range of not less than 700 nm and not more than 850 nm.

7. The method according to claim 1, further comprising:
a detecting step of detecting at least one of an end of the layered film and a defect on the basis of the transmitted-light intensities.

8. A method for producing a layered film including a base film and an applied layer on the base film,
the method comprising:
each step included in a method according to claim 1; and
a coating step of controlling the mass per unit area of the applied layer on a basis of the mass per unit area which mass has been calculated in the calculating step.

9. A method for producing a layered film including a base film and an applied layer on the base film,
the method comprising:
each step included in a method according to claim 1; and
a removing step of removing a per-unit-area-mass abnormal portion of the layered film on a basis of the mass per unit area which mass has been calculated in the calculating step.

10. A method for measuring a mass per unit area of an applied layer in a layered film including a base film and the applied layer provided on the base film,
the method comprising:
a light-transmitting step of causing measurement light to be transmitted through the layered film;
a light-measuring step of (i) separating, into a first beam having a first wavelength and a second beam having a second wavelength different from the first wavelength, the measurement light having been transmitted through the layered film and (ii) measuring respective transmitted-light intensities of the first and second beams; and
a calculating step of calculating the mass per unit area of the applied layer on a basis of the transmitted-light intensities.

* * * * *